United States Patent [19]

Hara et al.

[11] Patent Number: 4,930,890
[45] Date of Patent: Jun. 5, 1990

[54] METHOD AND APPARATUS FOR DETECTING THROUGH-HOLE VOIDS IN MULTI-LAYER PRINTED WIRING BOARD

[75] Inventors: Yasuhiko Hara, Machida; Kenzo Endo, Hadano, both of Japan

[73] Assignee: Hitachi Ltd., Tokyo, Japan

[21] Appl. No.: 210,097

[22] Filed: Jun. 22, 1988

[30] Foreign Application Priority Data

Jun. 25, 1987 [JP] Japan ................................. 62-156555

[51] Int. Cl.$^5$ ............................................ G01N 21/88
[52] U.S. Cl. ..................................... 356/241; 356/237
[58] Field of Search ................................. 356/237, 241

[56] References Cited

U.S. PATENT DOCUMENTS

| | | | |
|---|---|---|---|
| 4,145,714 | 3/1979 | MacDonald et al. | 356/241 |
| 4,538,909 | 9/1985 | Bible et al. | 356/237 |
| 4,679,938 | 7/1987 | Flamholz | 356/237 |

FOREIGN PATENT DOCUMENTS 6085596 10/1983 Japan .

OTHER PUBLICATIONS

Ernst A. Gutbier, "A New Method of Inspecting Plated-Through-Hole Connections", Processing Technical Program Natl., Electron Packaging Production Conference, Vol. 1974, pp. 56–62, (1974).

*Primary Examiner*—Davis L. Willis
*Assistant Examiner*—S. A. Turner
*Attorney, Agent, or Firm*—Fay, Sharpe, Beall, Fagan, Minnich & McKee

[57] ABSTRACT

A method and apparatus for detecting through-hole voids in a multi-layer printed circuit board. The through-hole is formed with an electrical conductor for interconnecting wiring patterns of upper layers and wiring patterns of lower layers of the printed wiring board and is illuminated with a beam having a wavelength falling within a specified wavelength band capable of exciting an luminescent beam from a layer material. The layer material is exposed by a through-hole void in the through-hole of the printed wiring board. The luminescent beam excited by the illumination beam impinging upon the layer material by way of the through-hole void in the through-hole is focussed by means of a focussing optical system and a photoelectric converter. The photoelectric converter converts the luminescent beam into an electrical signal. The presence of a through-hole void is indicated by the electrical signal.

22 Claims, 8 Drawing Sheets

FIG. IIA
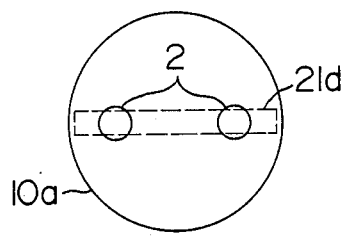
FIG. IIB
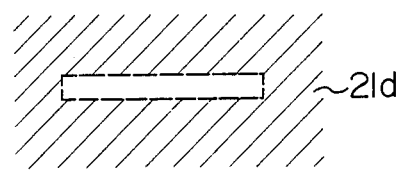
FIG. I2A
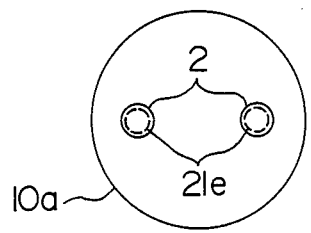
FIG. I2B
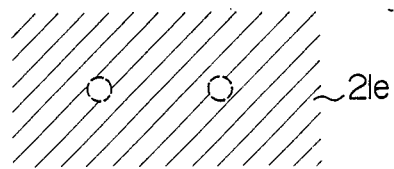

METHOD AND APPARATUS FOR DETECTING THROUGH-HOLE VOIDS IN MULTI-LAYER PRINTED WIRING BOARD

BACKGROUND OF THE INVENTION

This invention relates to automatic detecting of through-hole voids in a printed wiring board of multi-layer structure and more particularly to a through-hole void detect method and apparatus suitable for detecting through-hole voids in a multi-layer printed wiring board with high reliability.

In order to electrically interconnect layers in a multi-layer printed wiring board, a film of, for example, copper is formed on the inner wall of a through hole through an electroless plating process. A solder film is then formed on the copper film through an electrolytic plating process.

In a multi-layer board, the diameter of the through hole becomes small and the depth becomes large in proportion to an increase in the packing density of parts carried on the multi-layer printed wiring board and an increase in the number of layers. Under these circumstances, the formation of the plating films on the inner wall of the through hole can not easily be achieved. Additionally defective electrical conduction results if the through holes are not plated.

Such a defect is difficult to detect in the initial phase of production unless the defect is detected and corrected, though the defect will result in operation failure which could be fatal.

It is important to detect and remove defects of abnormal deposition of plated copper on the inner wall of a through hole in the initial stages of production. Defects of this type are hereinafter referred to as through-hole void defect.

In the past, a through-hole void check detecting method as disclosed in, for example, JP-A-60-85596 had been proposed in which a photosensitive plate or film is bonded to one surface of a board to cover substantially all through holes to be checked. The one surface of the board is then exposed to light in such a way that light illumination can pass through all of the through holes to be checked. Finally, the thus treated photo-sensitive plate or film is used as a light-shielding mask to perform through hole check.

According to another reported method disclosed in, for example, Processing Technical Program Natl, Electron Packaging Production Conference, Vol. 1974, pp 56–62 (1974), the layer material is mixed with a luminescent material. A luminescent beam, generated at a through-hole void under the irradiation of ultraviolet ray, is observed or measured. More specifically, the layer material is mixed with a luminescent coloring matter which can be excited by an exciting beam of 350 mm wavelength to generate or luminesce with a luminescent beam of 472 mm wavelength. A filter for passing a beam of 350 mm wavelength is supported above an ultraviolet ray lamp. A printed wiring board to be checked is supported horizontally above the filter and a second filter for absorbing the 350 mm wavelength ultraviolet ray is supported above the printed wiring board. The lower filter, printed wiring board and upper filter are suitably spaced apart from each other.

When the ultraviolet ray emitted from the lowermost ultraviolet ray lamp irradiates the lower filter, in the presence of a through-hole void in a through hole, the ultraviolet ray impinges upon a portion of the printed wiring board by way of the through-hole void to generate a luminescent beam. The operator viewing the upper filter from above can see the defective through hole with the through-hole void shine bright and can detect the through-hole void.

With this prior art method, only relatively large through-hole voids can presumably be detected.

The former prior art method faces the following problems.

First, one end of a through hole must be coverd completely in order that the illumination light can irradiate only the periphery of the through hole and can be prevented from entering the through hole. If one end of the through hole is covered incompletely, the presence of a through-hole void is erroneously recognized in spite of the fact that no through-hole void actually exists. In addition, when the number of through holes is large, troublesome open/close operation results.

Second, the light irradiating the periphery of the through hole must reach to the through hole by way of the interior of the board and the through hole void.

However, when the number of layers is large, the illumination light may be interrupted. In addition, the illumination light may also be intercepted by a circuit pattern which has already been formed on the outermost surface of the printed wiring board. As a result detecting of through hole voids often becomes impossible.

Last, when illumination light irradiates the other surface of printed wiring board opposite to the surface on which the photosensitive plate or film is mounted, it is difficult to prevent the illumination light from entering a through hole.

As regards the latter prior art, it was announced more than ten years ago but has not been adopted as a general method yet.

First, the layer material has to be mixed with the luminescent material. The additional step needed for mixing increases the cost and adversely affects the reliability of the layer material.

Second, the check is directed to a printed wiring board in which the through hole has a ratio of about 1:1 between its diameter and depth. It it is difficult for this prior art method to detect through-hole voids in a present-day printed wiring board in which the board has a thickness of several of millimeters, far larger than the diameter of the through hole being 0.3 to 0.5 mm.

In such a printed wiring board having small-diameter through holes, intensity of a luminescent beam passing through a small through-hole void is very small. Thus, the latter prior art method has difficulties in detecting through-hole voids.

SUMMARY OF THE INVENTION

An object of this invention is to provide through-hole void detecting method and apparatus based on luminescent phenomenon which can perform highly reliable detection of a small through-hole void by eliminating the need of mixing the layer material with any luminescent coloring matters and avoiding the influence of the configuration of inner-layer patterns of a printed wiring board.

According to the present invention, a photo-detection optical system is provided which detects a beam of a wavelength band generated from an object to be checked when a beam of a specified wavelength band irradiates the object. The beam of the specified wavelength band emitted from the photo-detection optical system is irradiated on a through hole in a printed wiring board standing for the object and is converted into the beam of the different wavelength band when it impinges upon a layer material of the printed wiring board by way of a through-hole void. The generated beam of the different wavelength band is detected by the photo-detection optical system which verifies the presence of a through-hole void.

The photo-detection optical system includes a lamp such as an extra high-pressure mercury arc lamp. An exciting beam of high intensity emitted from the lamp is collected by a collector lens and passed through an excitation filter to provide a wavelength of the exciting beam limited to a value within a wavelength band which is optimum for generation of a luminescent beam from the layer material of the printed wiring board. The exciting beam of the wavelength reaches a microscope objective lens. The microscope objective lens has so large a numerical aperture that the exciting beam is focused at a focusing angle of 10° or more to irradiate a through hole. The exciting beam is focused by the microscope objective lens on a point in the through hole whose inner wall is formed with a scattering surface. It is reflected repetitively at the scattering surface and diffused in the through hole to illuminate or irradiate the entire scattering surface.

In the presence of a through-hole void in the through hole, particularly, in the scattering surface, the exciting beam impinges upon the layer material of the printed wiring board by way of the through-hole void to generate a luminescent beam which scatters to the through hole. Since the luminescent beam has a wavelength falling within a wavelength band which is wider than that of the exciting beam and has no directivity, the luminescent beam is scattered to the through hole to provide scatterd luminescent beams of uniform intensity. Of the scattered luminescent beams, beams heading toward the photo-detection optical system are repetitively reflected at the scattering surface to reach the entrance of the through hole and are focused on a detector of the photo-detection optical system by means of the microscope objective lens. A dichroic mirror interposed between the microscope objective lens and the detector reflects the exciting beam emitted from the lamp and passes only the luminescent beam. An absorption filter interposed between the dichroic mirror and the detector then absorbs the wavelength band of the exciting beam while passing only the luminescent beam. Accordingly, the detector detects a bright image at the entrance of the through hole in the presence of a through-hole void but detects a dark image at the entrance of the through hole in the absence of any through-hole void, indicating that no luminescent beam is detected.

In this manner, any through-hole voids can be detected easily in a through hole.

When the size of the through-hole void is small, intensity of the luminescent beam from the through-hole void is very small, producing illumination of about $10^{-3}$ to $10^{-2}$ luxes on the surface of the detector. Therefore, an ordinary TV camera or linear image sensor cannot be used as the detector. In accordance with the invention, a particular TV camera such as a silicon intensifier target TV camera or an image intensifier TV camera capable of detecting a weak beam of intensity of $10^{-3}$ luxes or less may be used as the detector. Also, as the detector, a commercially available ultra-high sensitivity linear image sensor may be used wherein an image intensifier tube and an ordinary linear image sensor are used in combination.

The photo-detection optical system comprised of the microscope objective lens having a large numerical aperture and the ultra-high sensitivity detector is used to provide an exciting beam for generating a luminescent beam of a wavelength band different from that of the exciting beam in the presence of a through-hole void in a through hole and to detect the luminescent beam coming from the entrance of the through hole by means of the detector. The through-hole can readily be checked for voids with high reliability. This prevents the production of defective printed wiring boards. Consequently, operation failure of apparatus, such as computers, incorporating printed wiring boards is reduced.

BRIEF DESCRIPTION OF THE DRAWINGS

FIGS. 8A, 8B, 9A, 9B, 10A, 10B, 11A, 11B, 12A and 12B are diagrams for explaining the relation between the field of view of a microscope objective lens and the iris.

DESCRIPTION OF THE PREFERRED EMBODIMENTS

Figure 1:
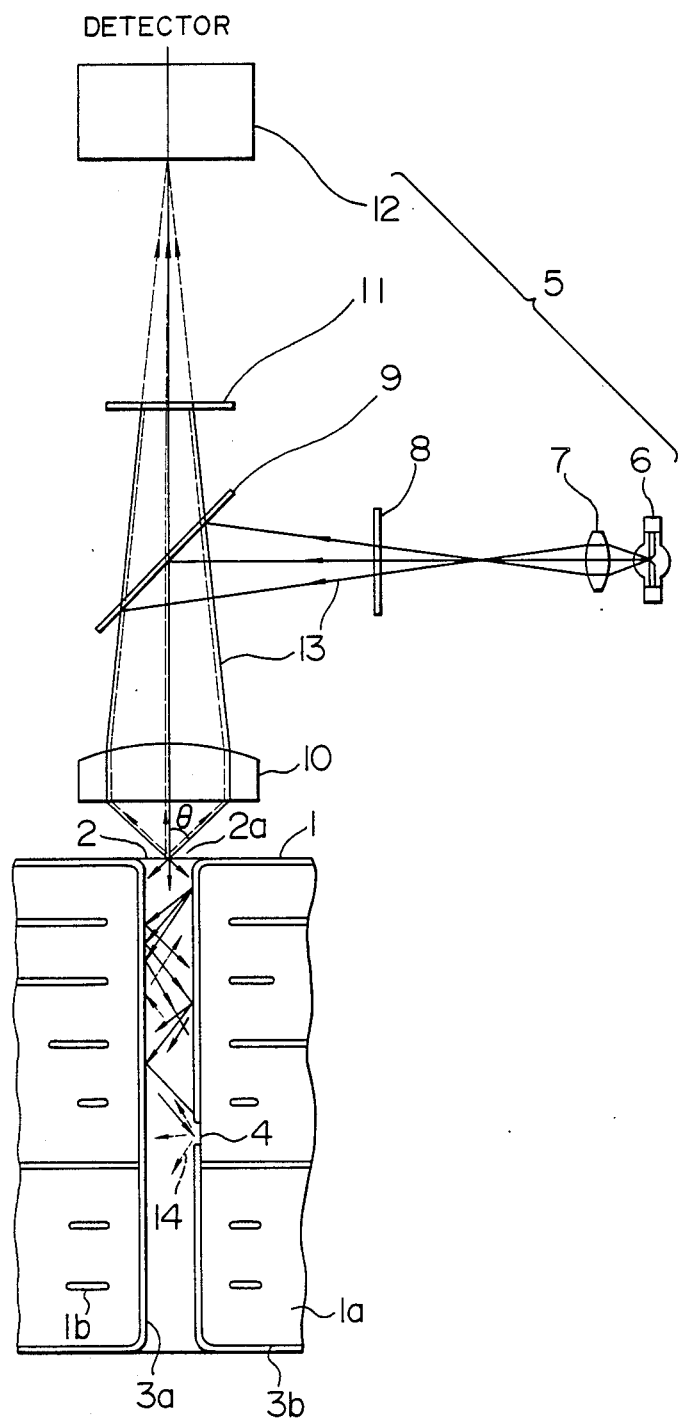
FIG. 1 is a schematic diagram illustrating a through-hole void detection apparatus according to an embodiment of the invention.

Referring now to FIGS. 1 and 2, a through-hole void detection apparatus according to an embodiment of the invention will be described.

As shown in FIG. 1, a printed wiring board 1 has a multi-layer structure in which each layer has a wiring pattern 1b. A through hole 2 is formed passing through the layers. The inner wall of the through hole 2 and the top and bottom surfaces of the printed wiring board 1 are covered with copper foils 3a and 3b, respectively. The copper foil 3a covering the inner wall of the through hole 2 has a scattering surface which can reflect an exciting beam 13 from a photo-detection optical system 5 to be described later. A portion of the copper foil 3a on the inner wall of the through hole 2 defectively peels off to form a defect, through-hole void 4.

Figure 2A:
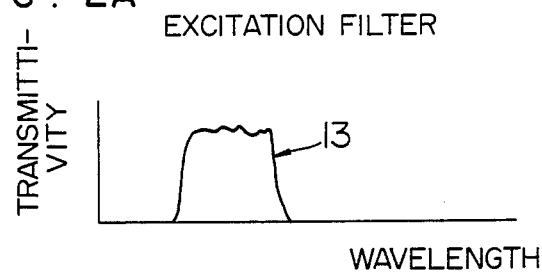
FIG. 2A is a graphic representation showing a transmission factor of an excitation filter.
Figure 2B:
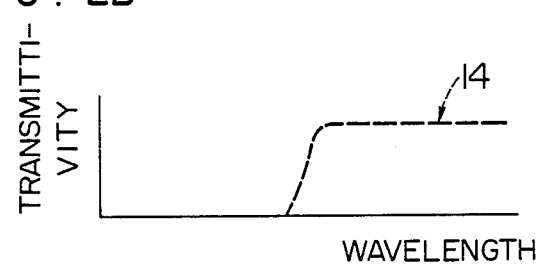
FIG. 2B is a graphic representation showing a transmission factor of a dichroic mirror.
Figure 2C:
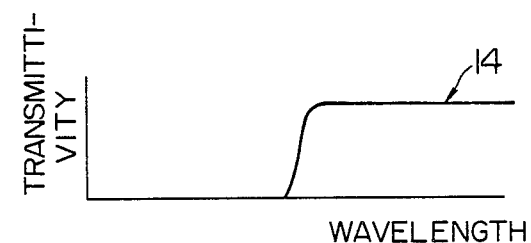
FIG. 2C is a graphic representation showing a transmission factor of an absorption filter.

The photo-detection optical system 5 comprises a lamp 6, a collector lens 7, an excitation filter 8, a dichroic mirror 9, a microscope objective lens 10, an absorption filter 11 and a detector 12. The lamp 6 is, for example, an extra high-pressure mercury arc lamp which can emit an exciting beam 13 of high intensity. The collector lens 7 collects the exciting beam emitted from the lamp 6. The excitation filter 8 can pass a wavelength of exciting beam 13 which is optimum for generating a luminescent beam 14 when it impinges upon a layer material 1a. Thus, only the exciting beam 13 of a wavelength limited to a value within a specified wavelength band as shown in FIG. 2A is permitted to pass through the filter 8. The dichroic mirror 9 can pass the luminescent beam 14 (having a longer wavelength than that of the excited beam 13) while reflecting the exciting beam 13, as shown in FIG. 2B. The microscope objective lens 10 has a large value of numerical aperture $NA = \sin \theta$. The lens 10 has a focusing angle $\theta$ of 10° or more for the excited beam 13 and luminescent beam 14 shown in FIG. 1 to set up $NA \geq \sin 10°$ so that the luminescent beam 14 coming from the through hole 2 can be focused sufficiently. The absorption filter 11 can absorb the wavelength band of the exciting beam 13 and pass only the luminescent beam 14, as shown in FIG. 2C. The detector 12 is, for example, a silicon intensifier target TV camera or an image intensifier TV camera of ultra-high sensitivity which can detect a very weak luminescent beam of $10^{-3}$ to $10^{-2}$ luxes or less. The detector 12 may also be of a linear image sensor type, particularly, a commercially available ultra-high linear image sensor wherein an image intensifier tube and an ordinary linear image sensor are used in combination. The luminescent beam 14 generated when the exciting beam 13 impinges upon the layer material 1a has no directivity and scatters uniformly from the through-hole void 4 to the through hole 2.

A method of detecting a through-hole void, is carried out using the through-hole void detection apparatus of the above construction, as will be described below.

An exciting beam 13 emitted from the lamp 6 is collected by the collector lens 7. A wavelength of exciting beam 13 limited to a wavelength band shown in FIG. 2A can be passed through the excitation filter 8. The output beam from the filter 8 is reflected by the dichroic mirror 9 and focused on a point in the through hole 2 by means of the microscope objective lens 10 objective lens 10 represents a focusing optical system having the large value of numerical aperture NA to establish $NA \geq \sin 10°$, so that the exciting beam 13 may sufficiently diffuse in the through hole 2 to irradiate the entire area of the surface of the copper foil 3a.

In the presence of a through-hole void 4 in the through hole, the exciting beam 13 impinges upon the layer material 1a of the printed wiring board 1 through the through-hole void 4. The luminescent beam 14 generated from the layer material 1a scatters to the through hole 2 by way of the through-hole void 4. Of scattered luminescent beams 14, beams heading upwards are repetitively reflected at the surface of the copper foil 3a to reach an entrance 2a of through hole 2 and focused on the detector 12 by means of the microscope objective lens 10' representing the focusing optical system. The dichroic mirror 9 reflecting the exciting beam 13 passes only the luminescent beam 14, as shown in FIG. 2B. Since the absorption filter 11 absorbs the wavelength band of exciting beam 13 while passing only the luminescent beam 14, as shown in FIG. 2C, the detector 12 detects a bright image at the entrance 2a of through hole 2 in the presence of a through-hole void 4 in through hole 2 but detects a dark image at the entrance 2a of through hole 2 in the absence of any through-hole void 4, indicating that no luminescent beam is detected. The detector 12, formed of a linear image sensor of ultra-high sensitivity, detects a luminescent beam of weak intensity which is $10^{-3}$ to $10^{-2}$ luxes or less.

Other embodiments of the invention will now be described.

Figure 3:
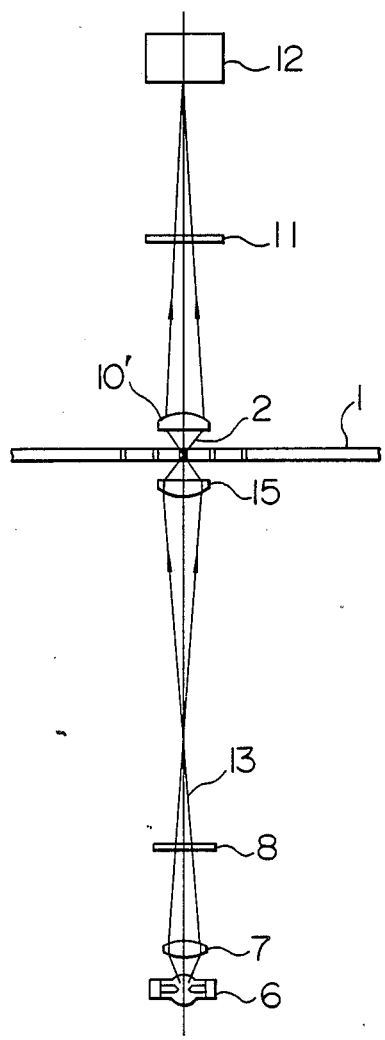
FIG. 3 is a schematic diagram illustrating a through-hole void check apparatus according to another embodiment of the invention.

Referring to FIG. 3, another embodiment of the invention shown therein comprises a lamp 6 provided on one side of the printed wiring board 1 to oppose the detector 12 on the other side of the board 1 by way of through-hole 2. Obviously, this embodiment dispenses with the dichroic mirror 9 of the FIG. 1 embodiment but instead needs a condenser lens 15 serving as a condensing optical system capable of condensing the exciting beam 13. The condenser lens 15 has a large numerical aperture comparable to that of a microscope objective lens 10'.

Figure 4:
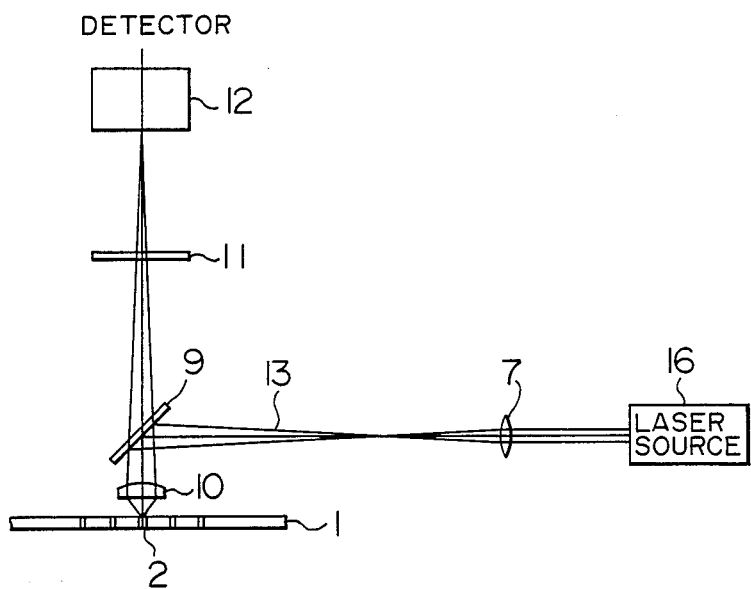
FIGS. 4 and 5 are schematic diagrams illustrating through-hole void detection apparatus according to further embodiments of the invention.

Referring to FIG. 4, another embodiment of the invention shown uses, as the exciting beam 13, a laser beam emitted from a laser source 16 and collected and broadened by means of the collector lens 7.

The laser source 16 can emit a single wavelength or a plurality of wavelengths limited to a specified wavelength band. Therefore, by using a laser source capable of emitting only a laser beam of the wavelength falling within the necessary exciting beam band, the excitation filter 8 of the FIG. 1 embodiment can be omitted.

Figure 5:
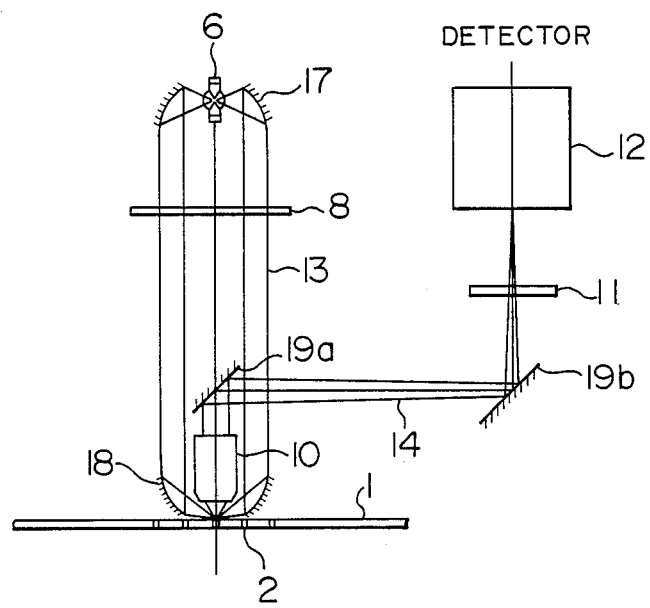

Referring to FIG. 5, a further embodiment of the invention wherein the manner of collecting the exciting beam is particularly considered is illustrated. The exciting beam incident on the printed wiring board has an incident angle equivalent to a numerical aperture of about 1 (one).

In this embodiment, an exciting beam 13, emitted from a lamp 6, is reflected downwards at a rotary-parabolic-surface reflection mirror 17 having rotary symmetry with respect to a line connecting the light source and a through hole. Reflected beams are collected by means of a similar rotary-parabolic-surface reflection mirror 18 disposed to oppose the reflection mirror 17 and a microscope objective lens 10 disposed inside the reflection mirror 18, so that a collected beam obliquely enters a through hole 2 in the printed wiring board 1 and is focused on portions in the through hole 2. More particularly, the rotary-parabolic-surface reflection mirror 18 forms an illuminating/focusing optical system which permits the exciting beam to impinge upon the entire inner circumference of the through hole, thus ensuring that exciting beams 13 of high intensity are scattered obliquely downwardly in the through hole. When a luminescent beam 14 is generated in the presence of a through-hole void (not shown) in the through hole 2, the luminescent beam 14 coming from the through hole 2 is focused on the detector 12 by means of two reflection mirrors 19a and 19b while being passed through the excitation filter 11, capable of passing only the luminescent beam 14. In this embodiment, the dichroic mirror of the FIG. 1 embodiment can be omitted.

Accordingly, in this embodiment, the exciting beam 13 of high intensity obliquely enters the through hole 2 and is reflected obliquely with high efficiency in the through hole 2 to impinge upon the layer material through a fine through-hole void.

Figure 6:
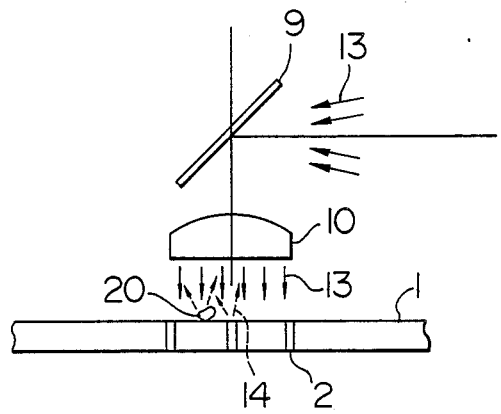
FIG. 6 is a diagram useful in explaining the detection of foreign matter on a printed wiring board.
Figures 7A, 7B:
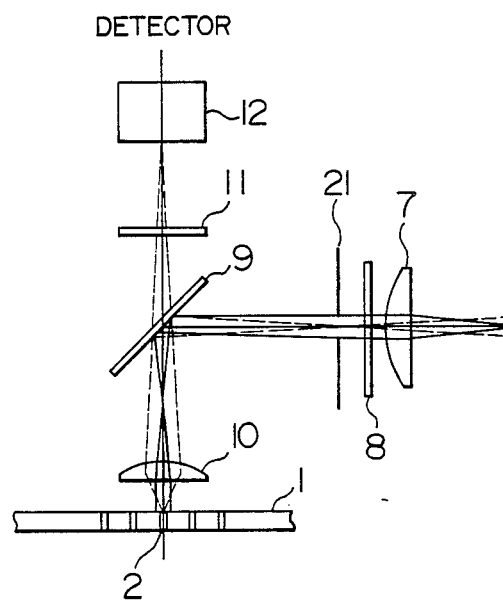
FIG. 7A is a schematic diagram illustrating a through-hole void detection apparatus according to a further embodiment of the invention.
FIG. 7B is a diagram for explaining an iris used in the FIG. 7A embodiment.

When a relatively wide area on the printed wiring board 1 is irradiated with the exciting beam 13, and on rare occasions, a foreign matter 20 is present within the area as shown in FIG. 6. The foreign matter 20 generates a luminescent beam 14 which leads to erroneous recognition that a spurious through-hole void is present in through hole 2. To prevent this problem, the illumination area on the printed wiring board 1 is reduced by restricting the exciting beam 13. For example, as shown in FIGS. 7A and 7B, an iris 21 is interposed between the excitation filter 8 and dichroic mirror 9 included in the photo-detection optical system 5 of the FIG. 1 embodiment to form an image of the exciting beam on the top surface of the printed wiring board 1.

Figure 8A:
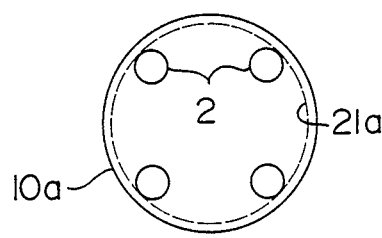
Figure 8B:
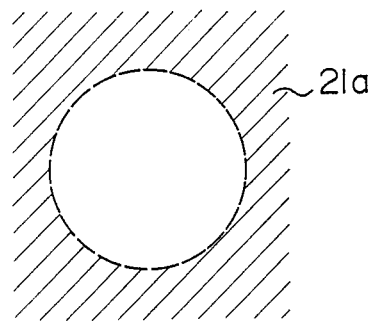
Figure 9A:
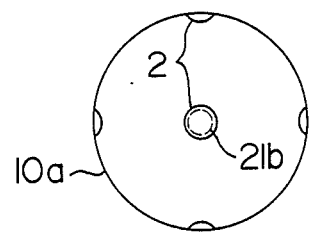
Figure 9B:
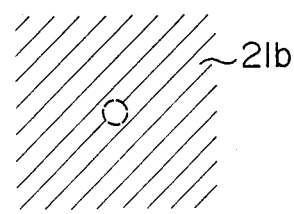
Figure 10A:
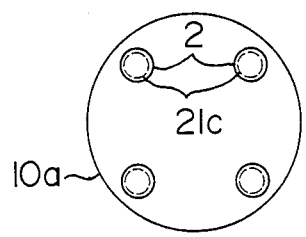
Figure 10B:
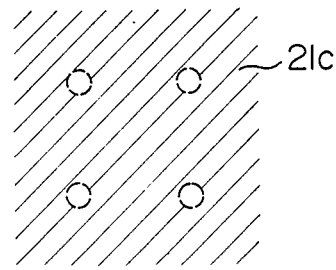

In particular, FIGS. 8A and 8B illustrate an instance where the iris is, a relatively large circular iris 21a. Circular iris 21a is slightly smaller than a field of view 10a of the microscope objective lens 10. In this case, the entire field viewed by the microscope objective lens 10 is irradiated with the exciting beam 13. FIGS. 9A and 9B illustrate an instance where a small circular iris 21b is used to permit the exciting beam 13 to irradiate only one through hole 2. FIGS. 10A and 10B illustrate an instance where an iris 21c having a plurality of small apertures, is used to irradiate a plurality of through holes 2 simultaneously.

Therefore, by using an iris 21 of suitable configuration, mistaking a foreign matter 20 for a through-hole void can be avoided in the event that the foreign matter 20 is present on the surface of printed wiring board 1.

The configuration of the iris has been described with reference to FIGS. 8A, 8B, 9A, 9B, 10A and 10B on the assumption that a TV camera is used as the detector 12. When a linear image sensor is used as the detector 12, an elongated iris 21d, as shown in FIGS. 11A and 11B, is used to irradiate only the portion to be detected by the linear image sensor. An iris 21e, having a plurality of apertures at positions corresponding to through holes 2 as shown in FIGS. 12A and 12B, is used to irradiate only the through holes 2.

In FIGS. 8A, 8B to FIGS. 12A, 12B, the iris 21 is described as being circular and oblong but the configuration of the iris 21 is not limited thereto and may be, for example, square and oval.

In giving the description with reference to FIGS. 1 to FIG. 12B, the printed wiring board 1, without a pattern on the outermost layer and available before etching is handled as the object to be checked. Since the entire printed wiring board 1, available before etching, is covered with a copper foil, the detector 12 will detect a luminescent beam 14 only when a through-hole void 4 is present in a through hole in the printed wiring board 1, except in the rare case when a luminescent beam 14 is generated from foreign matter 20.

Therefore, it is easy to detect any through-hole voids 4 in the through-holes of the printed wiring board 1 available before etching.

Figure 13B:
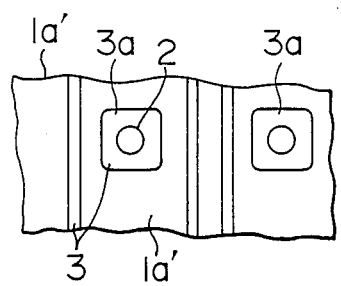
FIG. 13B is an enlarged fragmentary plan view showing the neighborhood of through holes in a printed wiring board shown in FIG. 13A.
Figure 13A:
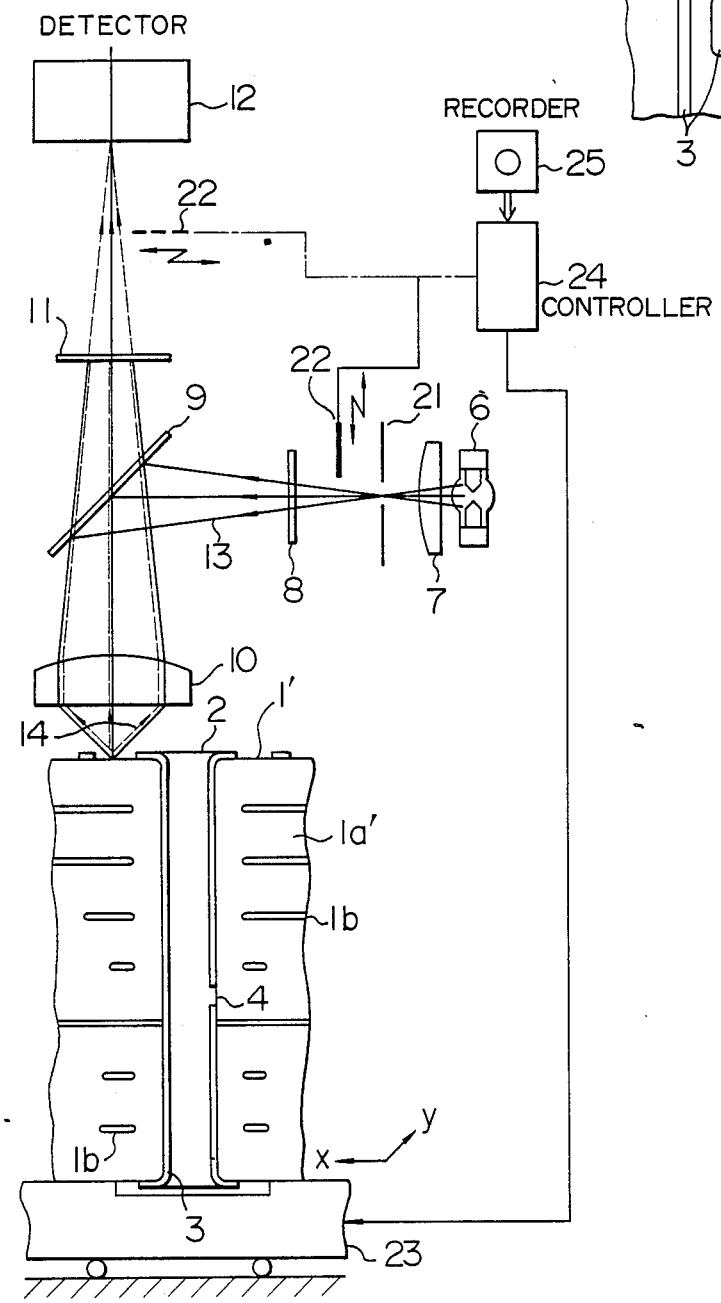
FIG. 13A is a schematic diagram illustrating a through-hole void detection apparatus according to a further embodiment of the invention.

Practically, however, a printed wiring board 1 with a pattern on the outermost layer and available after etching is sometimes handled as an object to be checked. In checking this type of printed wiring board 1, a luminescent beam 14 is generated when an exciting beam 13 impinges upon a layer material 1a' on printed wiring board 1' excepting a through hole 2, as shown in FIGS. 13A and 13B. The layer material 1a' is mistaken for a through-hole void 4 in a through hole 2. To solve this problem, in a further embodiment of the invention as shown in FIGS. 13A and 13B, an iris 21 is provided which restricts the illumination area to an area which is smaller than that of pad 3a. Pad 3a is copper foil formed on the outermost layer which is continuous to copper foil serving as an electrical conductor in a through hole 2. Between the iris 21 and the excitation filter 8, shutter 22 is interposed which is responsive to a commands from controller 24 to open and close. The controller 24 also controls driving of a table 23 which carries the printed wiring board 1' and which is driven by drive power fed from a drive source to move in X-axis and Y-axis directions on the horizontal plane parallel to the sheet of drawing of FIG. 3A. Thus, the shutter 22, responsive to the command from the controller 24, is intelocked with the movement of table 23 and is so controlled as to (1.) open, only when the focal position of excited beam 13 coincides with a point in the through hole 2 in the printed wiring board 1' and (2.) close, whenever the above condition is not satisfied. Incidentally, the position of any through holes 2 relative to a reference position on the printed wiring board 1' is represented by known variables which are obtained from design data. The design data is recorded on a recording device 25 and input to the controller 24. Accordingly, the controller 24 (1.) controls the movement of the table 23 carrying the printed wiring board 1' in accordance with the input design data, (2.) detects the time when the position of a through hole 2 coincides with the focal position of the objective lens 10, and (3.) commands the shutter 22 to open at the time of coincidence. In an alternative, the shutter 22 may be provided in association with the optical system for detecting the luminescent beam, as indicated at the phantom line in FIG. 13A. By using a strobe light source capable of emitting the excited beam, the shutter 22 can be omitted. However, because of a need for an exciting beam of high intensity, the extra high-pressure mercury arc lamp 6 and the shutter 22 may preferably be used in combination. The light source in the form of a laser source can be turned on and off easily by using an acoustic optic reflector or the like.

In detecting through-hole voids after the formation of the outermost layer pattern (after etching), a luminescent beam of high intensity is generated when the exciting beam impinges upon a layer of material from which copper has been removed. Detector 12 of ultra-high sensitivity is damaged by receiving the high intensity luminescent beam. The detector 12 must be protected from the reception of the intensive luminescent beam.

With the detection apparatus shown in FIGS. 13A and 13B, the detection of the through-hole void can be effected in substantially the same manner as described previously in connection with the preceding embodiments and will not be described herein.

As described above, according to the invention, the through-hole void in the presence of a through hole can readily be detected with high reliability to prevent the production of defective printed wiring boards and failure of apparatus such as computers incorporating printed wiring boards.

We claim:

1. A method of detecting a through-hole void existing on a surface of a through-hole which is formed with an electrical conductor for interconnecting wiring patterns of upper layers and wiring patterns of lower layers in a multi-layer printed circuit board comprising the steps of:

emitting an exciting beam having a wavelength limited to a value within an optimum wavelength band which is capable of exciting a fluorescent light through said through-hole void from a layer material which is exposed at the through-hole void;

focusing said exciting beam over said through-hole and illuminating said through-hole with said exciting beam by a focusing/illuminating optical system in which said exciting beam has an incident angle which is not less than 10° in order to let said exciting beam reflect many times between said surface of said through-hole such that said exciting beam impinges upon said layer material in an almost horizontal direction through said through-hole void;

converging said fluorescent light emitted into said through-hole from said through-hole void, by means of said focusing optical means at an illuminating side;

filtering said fluorescent light; and, detecting said through-hole void for its presence on the basis of an electrical signal converted by a photoelectric conversion means which detects said converged fluorescent light after filtering.

2. A method of detecting a through-hole void according to claim 1 wherein an electrical conductor is formed on the entirety of at least one surface of said multi-layer printed circuit board.

3. A method of detecting a through-hole void according to claim 1 wherein said exciting beam is focused into a beam spot, said beam spot having a size smaller than the size of a pad at which said through-hole if formed.

4. A method of detecting a through-hole void according to claim 1 wherein positioning of said exciting beam on the through-hole is effected in accordance with the design data and thereafter a shutter is opened to apply the illuminating beam to the positioned through-hole.

5. A method of detecting a through-hole void according to claim 1 wherein positioning of said illuminating beam on the through-hole is effected in accordance with the design data and thereafter a shutter is opened to permit said focusing optical system to converge said fluorescent light coming from the positioned through-hole on said photoelectric conversion means.

6. An apparatus for detecting a through-hole void existing on a surface of a through-hole which is formed with an electrical conductor for interconnecting wiring patterns of upper layers and wiring patterns of lower layers in a multi-layer printed wiring board comprising:

a light source means for emitting an exciting beam having a wavelength limited to a value within an optimum wavelength band which is capable of exciting a fluorescent light through said through-hole void from a layer material which is exposed at said through-hole void;

an illuminating/focusing optical system having a numerical aperture which is not less than sin 10° for focusing said exciting beam over said through-hole obliquely in order to let said exciting beam reflect many times between said surface of said though hole such that said exciting beam impinges upon said layer material in an almost horizontal direction through said through-hole void;

a fluorescent light detecting optical system for converging said fluorescent light at the illuminating side;

an absorption filter for passing only said fluorescent light emitted into said through-hole through said through-hole void from said layer material; and, a photoelectric conversion means for converting said focused fluorescent light detected through said absorption filter into an electrical signal which is used to detect said through-hole void for its presence automatically.

7. The apparatus for detecting a through-hole void according to claim 6 wherein said illuminating/focusing optical system further comprises a dichroic mirror for reflecting said exciting beam and for passing said fluorescent light.

8. The apparatus for detecting a through-hole void according to claim 6 wherein said light source comprises an extra high-pressure mercury arc lamp.

9. The apparatus for detecting a through-hole void according to claim 6 wherein said light source comprises a laser source.

10. The apparatus for detecting a through-hole void according to claim 7 wherein said illuminating/focusing optical system further comprises an excitation filter, interposed between said light source and said dichroic mirror, for passing a wavelength of said exciting beam.

11. The apparatus for detecting a through-hole void according to claim 6 wherein said illuminating/focusing optical system forms an object lens.

12. The apparatus for detecting a through-hole void according to claim 6 wherein said illuminating/focusing optical system comprises a rotary-parabolic-surface mirror for focusing the exciting beam and an object lens for converging the fluorescent light.

13. The apparatus for detecting a through-hole void according to claim 6 wherein said illuminating/focusing optical system comprises an iris for the exciting beam which makes the size of the exciting beam smaller than the size of the pad at which the through-hole is formed.

14. The apparatus for detecting a through-hole void according to claim 6 wherein said apparatus further comprises positioning means for positioning the through-hole of the multi-layer printed wiring board with relation to said illuminating beam in accordance with the design data.

15. The apparatus for detecting a through-hole void according to claim 14 wherein the illuminating/focusing optical system further comprises a shutter which is opened to apply to the exciting beam illumination to the through-hole which has completed its positioning by positioning means.

16. The apparatus for detecting a through-hole void according to claim 14 wherein the illuminating/focusing optical system further comprises a shutter which is opened to permit said photoelectric conversion means to detect the luminescent beam coming from the through-hole which has completed its positioning by positioning means.

17. The apparatus for detecting a through-hole void according to claim 6 wherein said photoelectric conversion means comprises an image intensifier.

18. The apparatus for detecting a through-hole void according to claim 6 wherein said photoelectric conversion means comprises an image intensifier TV camera.

19. The apparatus for detecting a through-hole void according to claim 6 wherein said photoelectric conversion means comprises a silicon intensifier target TV camera.

20. An apparatus particularly useful for detecting through-hole voids in through-holes of multi-layer printed wiring boards having small aspect ratios of through-hole diameter relative to circuit board thickness, wherein a through-hole void is detected at a side from which a detection process originates, comprising:

an exciting beam generating means for generating an exciting beam possessing a wavelength that will change when impinged upon wiring board material;

a first optical means for focussing and directing the exciting beam to enter the through-hole in a near horizontal direction whereby the exciting beam can reflect off the walls of the through-hole many times and allow the exciting beam to impinge the through-hole void in a near horizontal manner;

a second optical means for converging luminescent beams generated by the impingement of the exciting beam upon the wiring board material, said luminescent beams having a different wavelength than the exciting beam whereby the luminescent beam can be detected on the side of the multi-layer wiring board from which the exciting beam is generated;

a detecting means for detecting the luminescent beams, said luminescent beams indicating that a through-hole void is present in the through-hole.

21. The apparatus for detecting through-hole voids according to claim 20 further comprising a filter which discriminates between the exciting beam and the luminescent beam whereby the detecting means can easily detect whether a luminescent beam is present on the side of the wiring board from which the exciting beam is generated.

22. The apparatus for detecting through-hole voids according to claim 20 further comprising a dichroic mirror that reflects the exciting beam and passes the luminescent beam, whereby the generating means and the detecting means can be disposed on the same side of the wiring board.

* * * * *